United States Patent
Richter et al.

(10) Patent No.: US 12,042,616 B2
(45) Date of Patent: Jul. 23, 2024

(54) DEVICE FOR DEPOSITING AN ELEMENT BY MEANS OF A CANNULA

(71) Applicant: SFM MEDICAL DEVICES GMBH, Wächtersbach (DE)

(72) Inventors: Timo Richter, Linsengericht (DE); Olaf Brömsen, Mörfelden (DE)

(73) Assignee: SFM MEDICAL DEVICES GMBH, Wächtersbach (DE)

( * ) Notice: Subject to any disclaimer, the term of this patent is extended or adjusted under 35 U.S.C. 154(b) by 664 days.

(21) Appl. No.: 17/292,522

(22) PCT Filed: Nov. 19, 2019

(86) PCT No.: PCT/EP2019/081754
§ 371 (c)(1),
(2) Date: May 10, 2021

(87) PCT Pub. No.: WO2020/104430
PCT Pub. Date: May 28, 2020

(65) Prior Publication Data
US 2021/0393935 A1    Dec. 23, 2021

(30) Foreign Application Priority Data
Nov. 23, 2018    (DE) ..................... 10 2018 129 618.5

(51) Int. Cl.
*A61M 37/00* (2006.01)
*A61B 17/34* (2006.01)
(52) U.S. Cl.
CPC ..... *A61M 37/0069* (2013.01); *A61B 17/3468* (2013.01)

(58) Field of Classification Search
None
See application file for complete search history.

(56) References Cited

U.S. PATENT DOCUMENTS

| | | | | |
|---|---|---|---|---|
| 3,957,082 A | * | 5/1976 | Fuson | A61M 39/223 604/80 |
| 4,940,458 A | * | 7/1990 | Cohn | A61B 17/3401 604/512 |

(Continued)

FOREIGN PATENT DOCUMENTS

DE    10 2013 112 324 A1    5/2015

OTHER PUBLICATIONS

International Search Report, dated Feb. 26, 2020, corresponding to PCT/EP2019/081754.

(Continued)

*Primary Examiner* — Manuel A Mendez
(74) *Attorney, Agent, or Firm* — LADAS & PARRY LLP; Malcolm J. MacDonald, Esq.

(57) ABSTRACT

A device for depositing a solid medicament, having: a cannula (12) having a tip (18) provided at the distal end; and an attachment (20) which receives a proximal region of the cannula and has ridges (24, 26, 28) extending perpendicularly to the longitudinal axis of the cannula; and a plunger (16) which is movable progressively inside the cannula and has a handle (38). The handle (38) has rib-like retaining elements which extend in the longitudinal direction of the plunger (16), are spaced apart therefrom and are connected to the plunger in each case using a connecting element which can be severed at least in one of its end regions by interacting with the attachment (20).

26 Claims, 19 Drawing Sheets

(56) References Cited

U.S. PATENT DOCUMENTS

Figure 1:
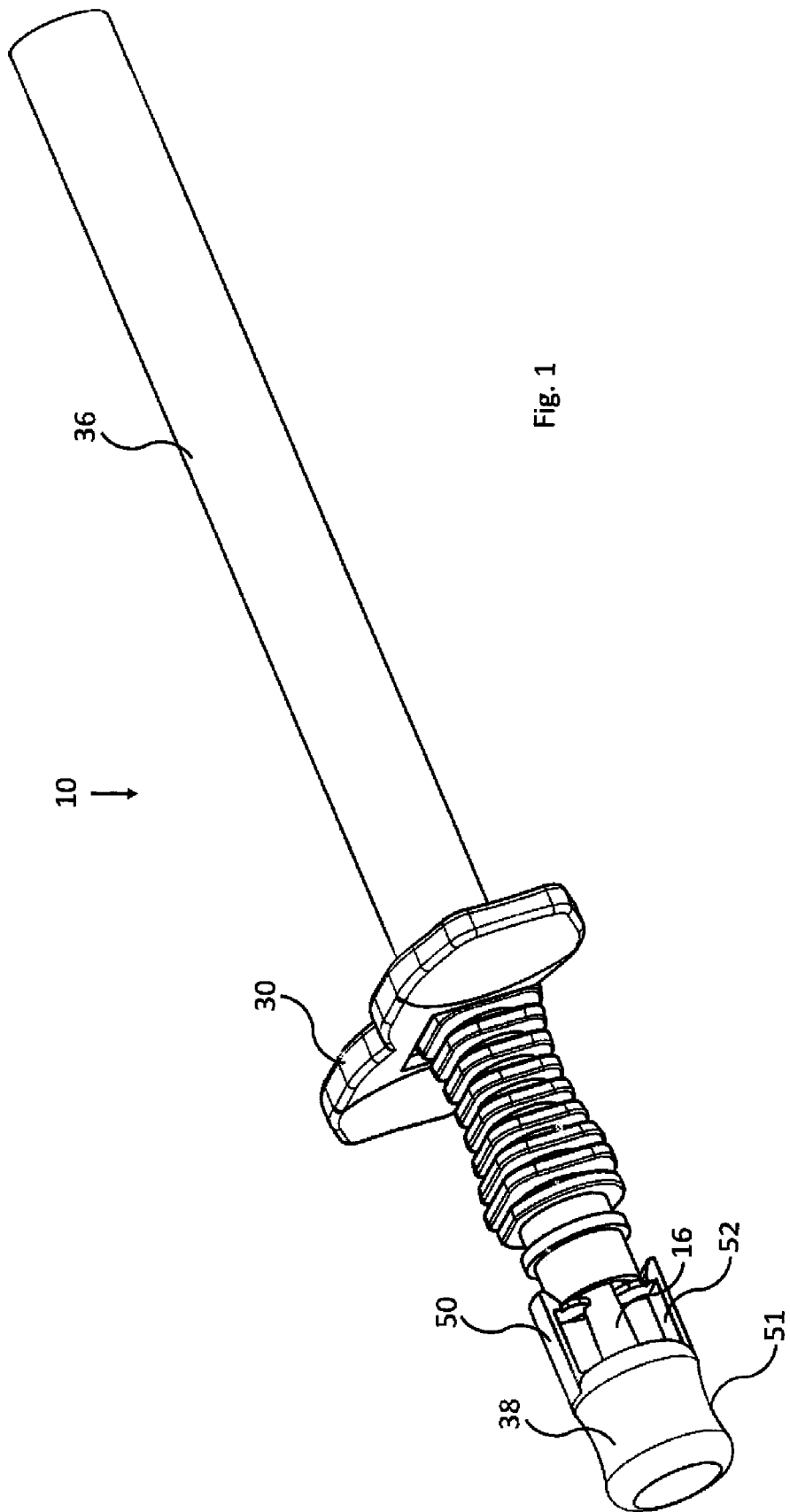

| | | | |
|---|---|---|---|
| 5,312,345 | A | 5/1994 | Cole |
| 5,538,378 | A * | 7/1996 | Van Der Drift ........ F16B 39/32 |
| | | | 411/300 |
| 5,810,769 | A | 9/1998 | Schlegel et al. |
| 11,246,574 | B2 | 2/2022 | Shabaz et al. |
| 2009/0131908 | A1 | 5/2009 | McKay |
| 2010/0256555 | A1 | 10/2010 | Birmelin et al. |
| 2011/0098675 | A1 | 4/2011 | Schmalz |
| 2015/0105719 | A1 * | 4/2015 | Haindl ............... A61B 17/3403 |
| | | | 604/165.02 |
| 2015/0297213 | A1 | 10/2015 | Lehtinen et al. |
| 2017/0065805 | A1 | 3/2017 | Tutera |
| 2018/0117263 | A1 * | 5/2018 | Cumbo ............... A61M 5/3287 |

OTHER PUBLICATIONS

Japanese Office Action, dated Aug. 23, 2022, corresponding to Japanese Application No. 2021-529026.

* cited by examiner

DEVICE FOR DEPOSITING AN ELEMENT BY MEANS OF A CANNULA

The invention relates to a device, in particular for depositing an element, such as a solid medicament or implant, comprising a cannula with a tip present at the distal end and an extension accommodating the proximal region of the cannula, which extension preferably has at least one rib extending transversely of, in particular perpendicularly to, the longitudinal axis of the cannula, and a plunger with a handle which is displaceable at least in part within the cannula.

In human and veterinary medicine, solid medicaments or implants, which may be tags, for example allowing animals to be identified or monitored, are deposited by means of injection devices. Such devices are known, for example, from WO 2013/167431 A1 or EP 2 314 342 A1. The plunger, which may also be denoted stylet, may possibly be fixed in place after the element has been deposited in order to protect the persons administering the elements, i.e. the cannula tip is covered by the plunger, such that there is no risk of injury.

DE 10 2012 104 058 A1 discloses a cannula with a displaceably arranged stylet from which originates a latching hook which engages in a recess of the cannula holder when the distal end of the stylet is covering the cannula tip.

DE 10 2013 112 324 A1 provides a cannula with a stylet which is fixed in position by interaction with the ground portion of the cannula.

US 2017/0065805 A1 discloses a trocar in which a stylet projects beyond the tip of a tube.

The object of the present invention is, inter alia, that of further developing a device of the initially stated type in such a manner that, when no further use is to proceed, protection is provided against injuries caused by the cannula tip. According to a further aspect, the device is intended to be usable repeatedly for depositing elements.

According to another aspect of the invention, it is also intended for it to be straightforwardly apparent to users whether the plunger is being or has been moved into a position in which the tip is to be or has been covered.

In order to achieve at least one of the aspects, the invention substantially provides that the handle of the plunger has a base portion which has tab-like retaining elements originating therefrom in the longitudinal direction of the plunger and extending spaced therefrom, and that each retaining element is connected to the plunger via a connecting element which is severable in at least one of the end regions thereof by interaction with the extension. In particular, it is provided that the connecting element is severably connected to the retaining element and articulatedly connected to the plunger or vice versa.

Such a design of the handle used for displacing the plunger firstly makes it possible for the retaining elements, which may also be denoted tongues, with the connecting elements connecting with the plunger, to act on the one hand as a limit stop, so as to enable repeated use, while, on the other hand, on application of force onto the handle in the direction of the distal portion of the cannula, separation from the retaining element proceeds, wherein, on further displacement of the plunger, the retaining elements, due to the connection, in particular articulated connection, which is still in existence, are oriented along the plunger by interaction with the extension, such that they cannot cause a hazard in the region of administration. At the same time, latching is effected by the quasi-hook-shaped retaining elements interacting with a latching receptacle, in particular the first rib, of the extension and engaging therebehind, such that uncontrolled withdrawal of the plunger from the cannula is ruled out. As a consequence, the tip thereof is permanently covered by the plunger.

In particular, it is provided that the retaining element has a distal latching portion extending in the direction of the plunger rod, such that a hook-shaped geometry is obtained.

In particular, it is provided that the connecting element is connected to the latching portion.

It is preferably provided that the connecting elements are articulatedly connected to the plunger, such that it is of course also possible for there to be an articulated connection to the retaining elements, wherein the connecting elements are separable from the plunger.

The invention also provides that the connecting elements are severable at both ends, i.e. on the one hand in the connecting region with the retaining elements and on the other hand with the plunger.

In order to ensure reliable and straightforward separation of the connecting element from the latching element, the invention further provides that the extension has a proximal hollow-cylindrical portion with an external diameter D and that the clearance between two latching portions diametrically opposed with regard to the longitudinal axis of the plunger rod is equal to or approximately equal to D. Thus, on displacement of the plunger in the direction of the extension, the hollow-cylindrical portion acts directly on the respective connecting region between the connecting element and the retaining element, such that straightforward separation is possible. The opposite side is connected via a film hinge to the plunger itself such that, on further movement of the plunger into the cannula, the connecting elements rest against the plunger and pass into the interspace between the hollow-cylindrical portion and the plunger.

An independent proposed solution provides that the handle is connectable to the extension via a screw connection and the length of the plunger is matched with the length of the cannula in such a way that in a first position, in which in the absence of a screw fastening but with the extension and the handle in contact, the tip of the plunger is uncovered, and that in a second position, in which the extension and the handle are screwed together, the distal end region of the plunger covers the tip.

The invention is in particular distinguished in that, in the second position, the extension and the handle are latched together. Latching may here be configured such that it is haptically and/or acoustically perceptible.

In order to screw the handle and extension together, it is also possible for the handle to have an external thread which interacts with an internal thread present in the extension.

The invention alternatively provides that the handle has an internal thread which interacts either with tabs, such as Luer Lock tabs, projecting out from the extension, in particular from the proximal edge region thereof, or with an external thread of the extension.

The base portion of the handle of the plunger preferably has a circumferentially cylindrical geometry. It is in particular provided that the circumferential wall of the base portion has a smaller diameter in the central region than in the end regions thereof, such that it can be easily grasped.

The retaining elements may on the outside transition flush into the circumferential surface of the base portion.

The handle itself may be a plastics injection moulding.

Depending on whether the cannula is to be used to deposit a solid medicament or an implant or a succession of a plurality of such elements, the teaching of the invention is intended to ensure that, once the cannula has been used, i.e.

after it has been removed from a living organism, the cannula tip is covered in such a way that any risk of injury is prevented.

The extension of the cannula and handle of the plunger, which may also be denoted stylet, may be structurally configured such that two defined positions of limit stop and extension are haptically and/or acoustically perceptible.

In the position of the plunger in which the cannula tip is uncovered, a limit stop counters any further displacement of the plunger in the direction of the tip of the cannula. This limit stop may be formed by the connecting elements between the retaining elements and the plunger Alternatively, the limit stop is provided by interaction of the handle and limit stop before they are screwed together. If the cannula tip is to be covered, the limit stop is overcome and in particular the extension and handle latch in a second predetermined position, either by interaction of the retaining elements with latching elements such as a rib of the extension or by overcoming a projection such as a shoulder during screw fastening.

Figure 2:
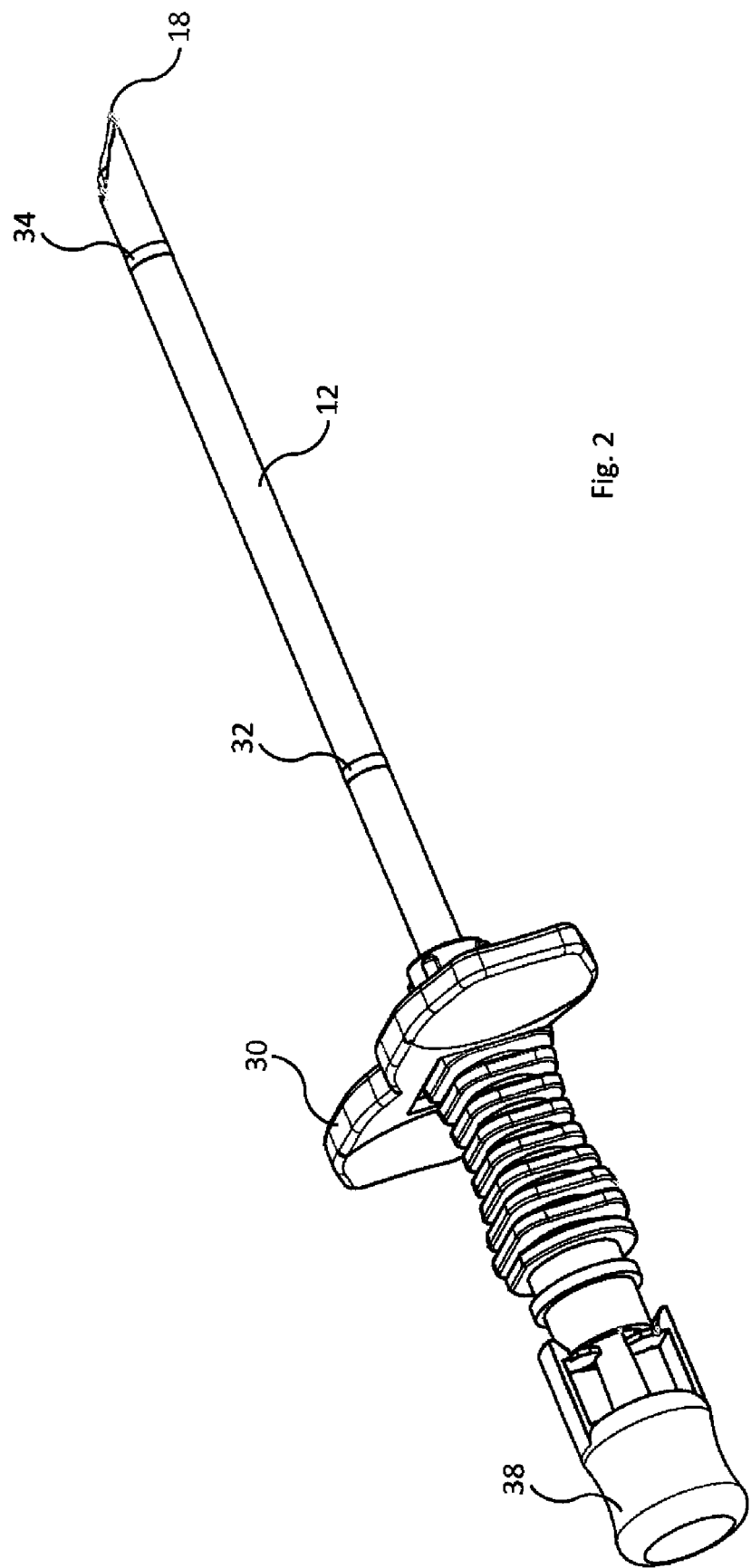
Figure 3:
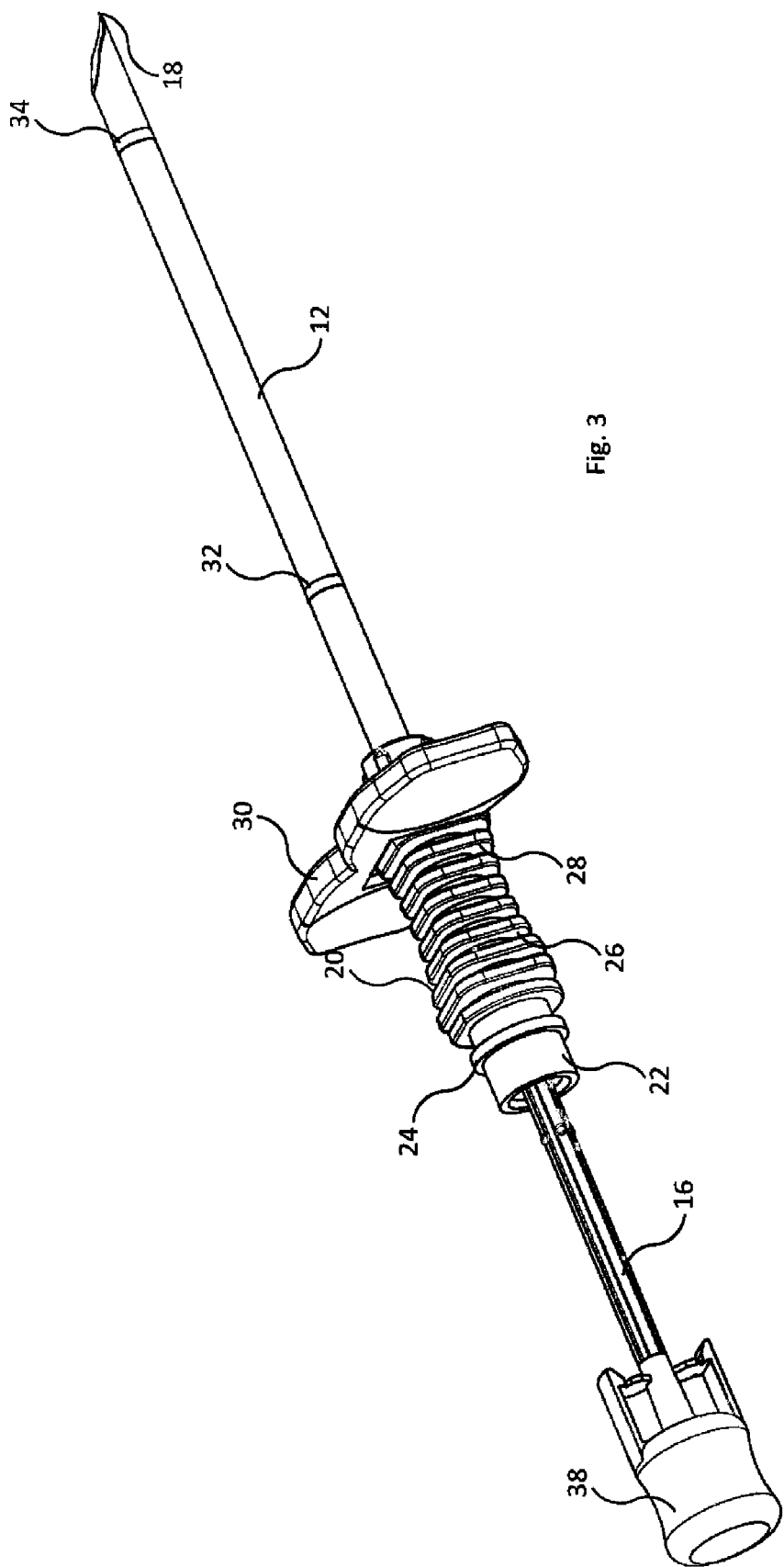
Figure 4:
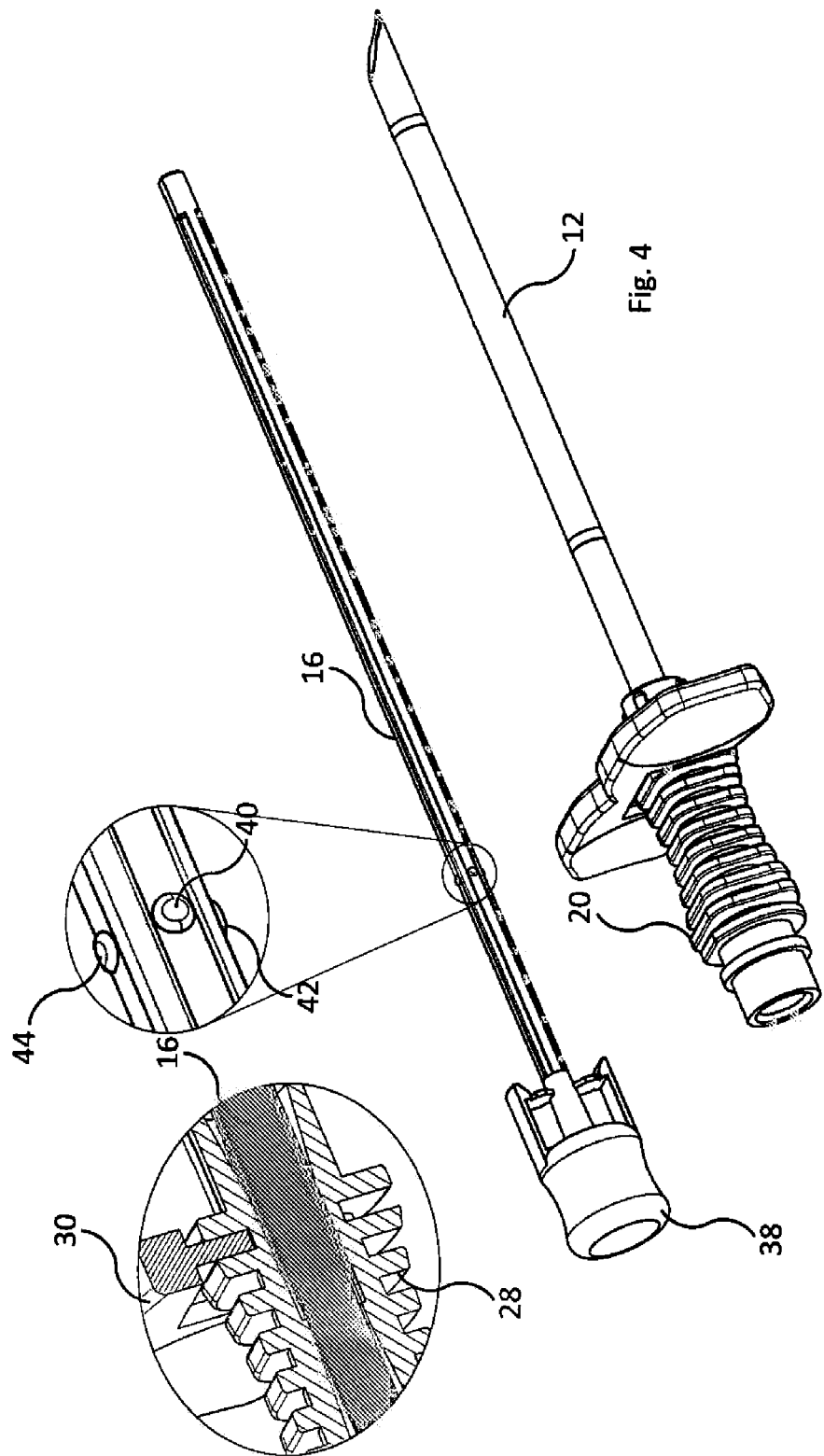
Figure 5:
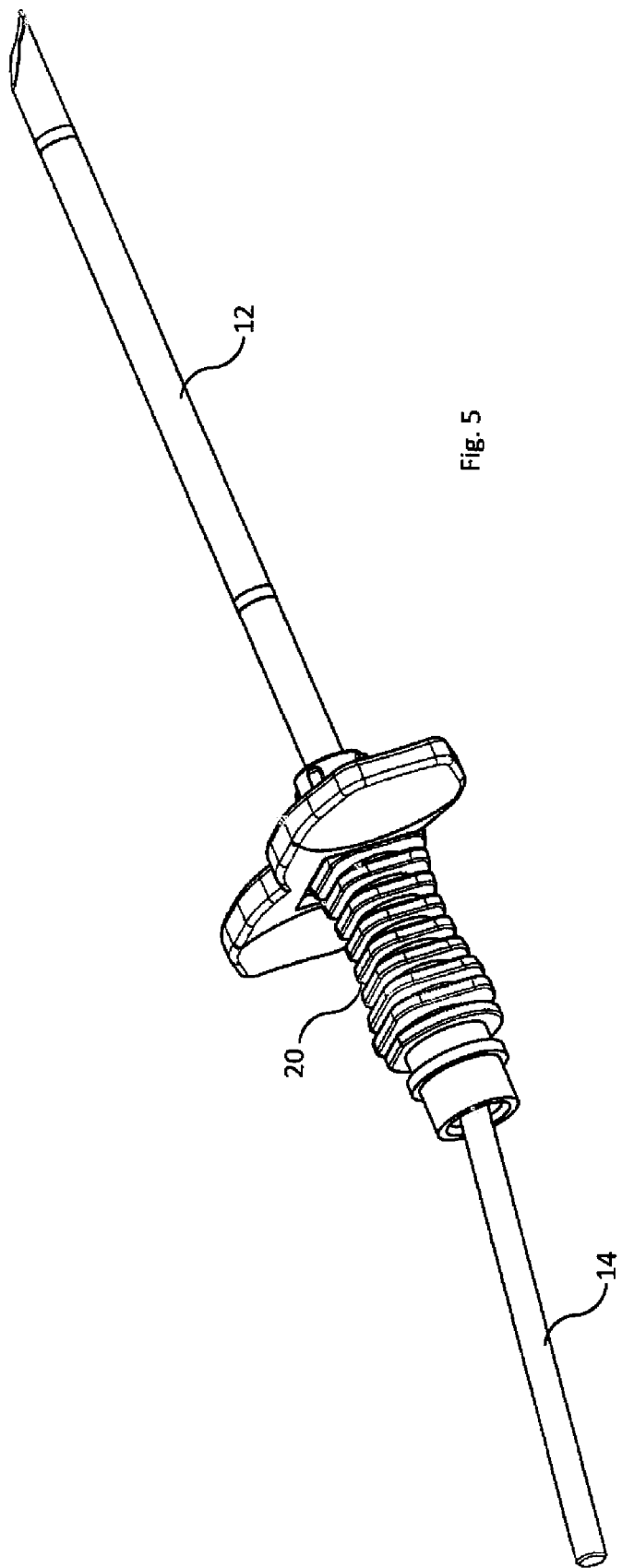
Figure 6:
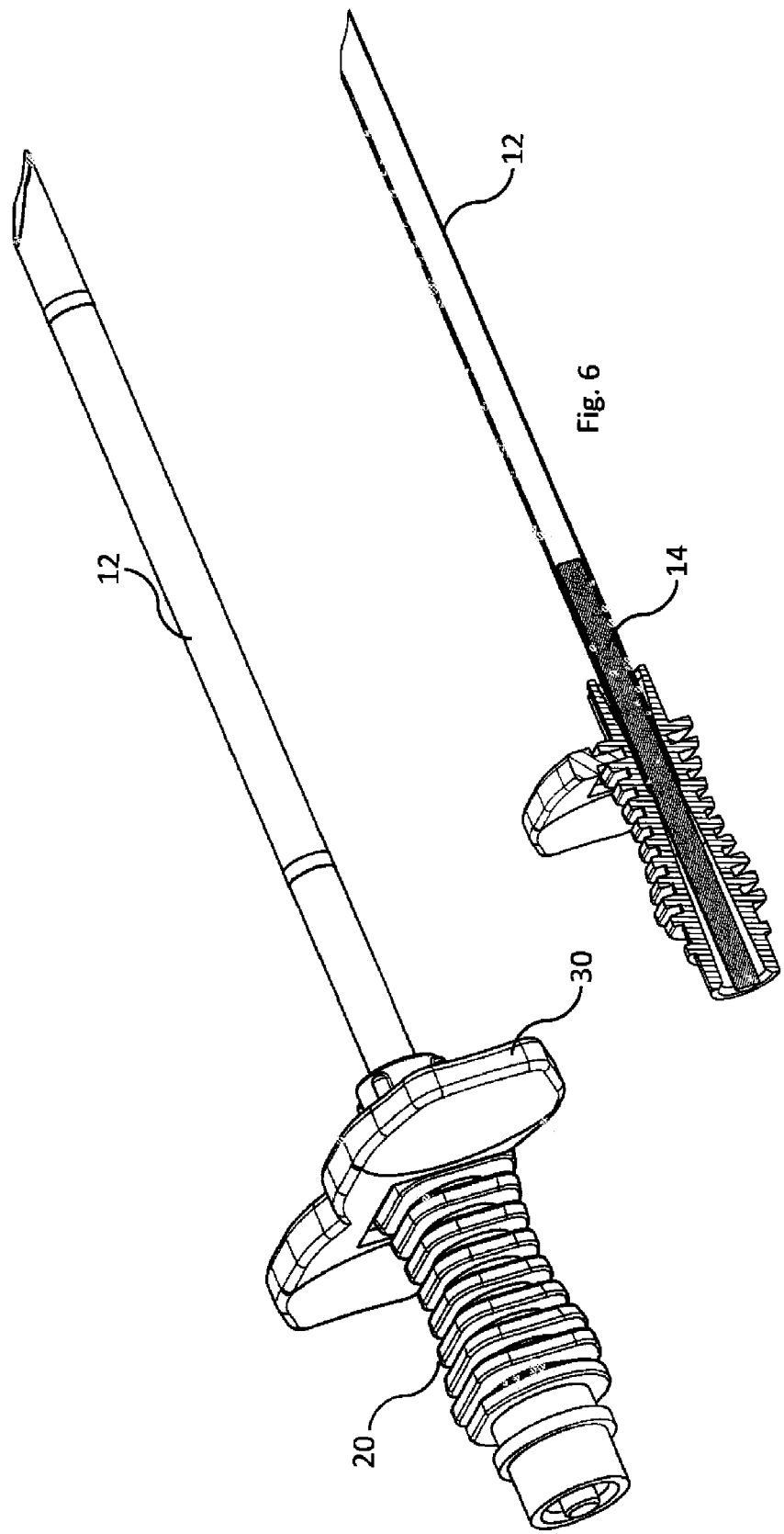
Figure 7:
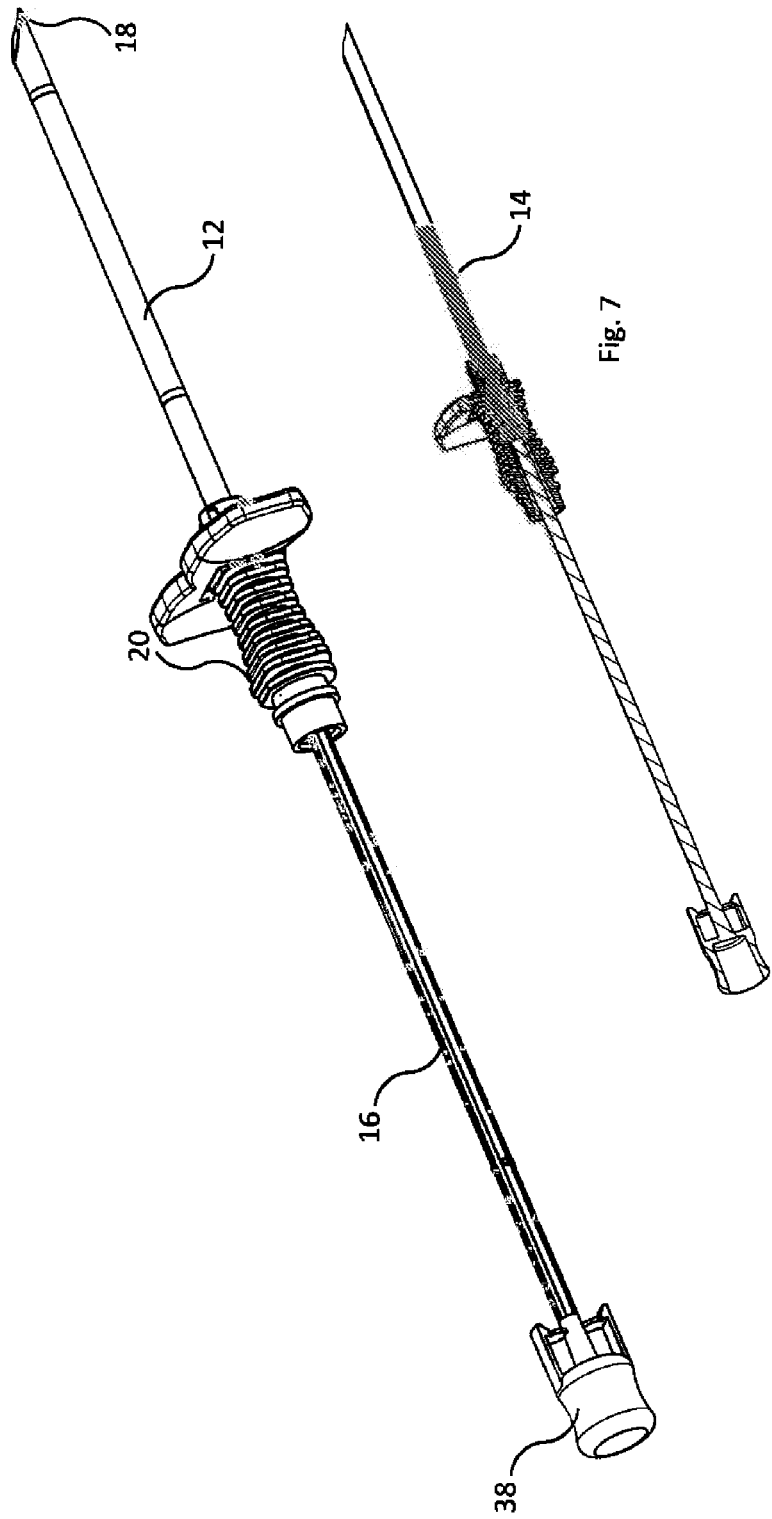
Figure 8:
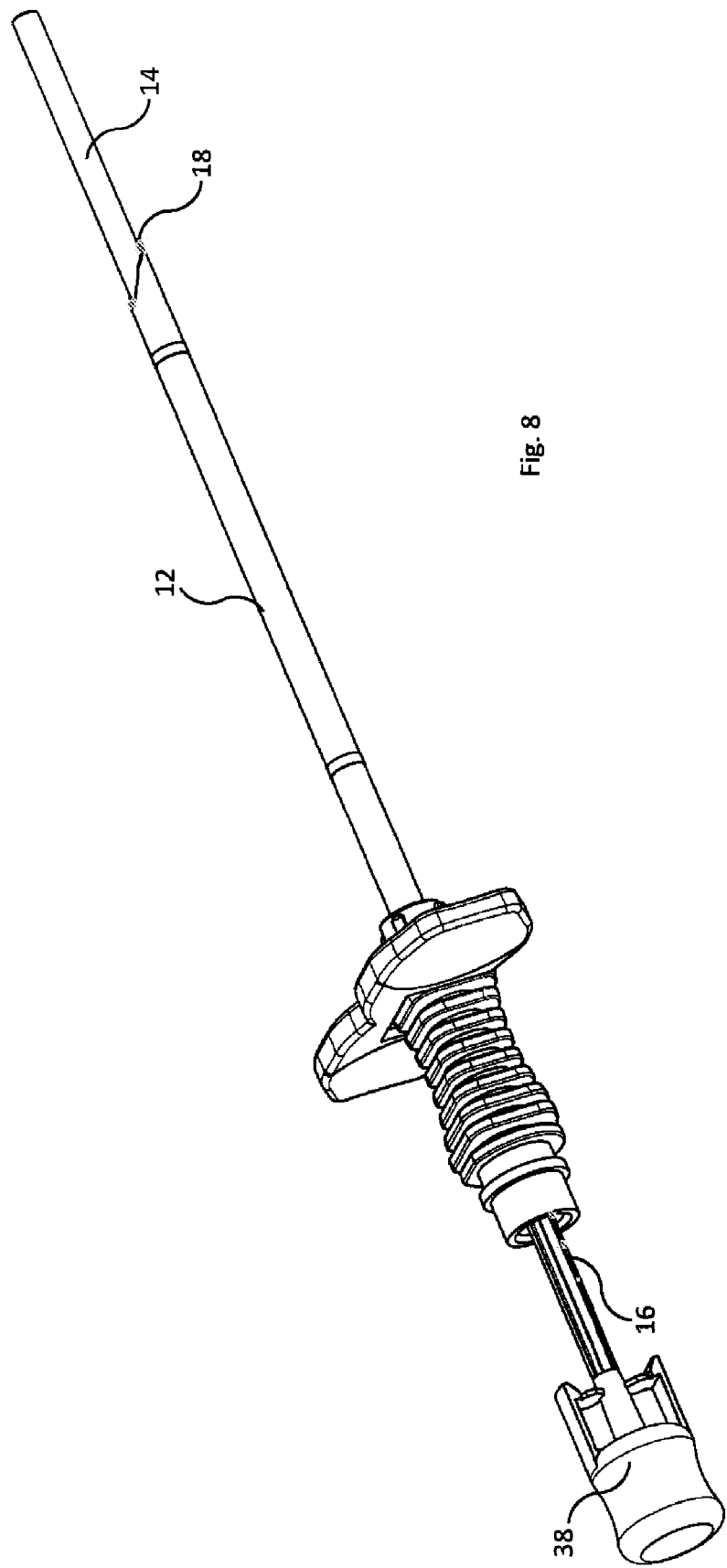
Figure 9:
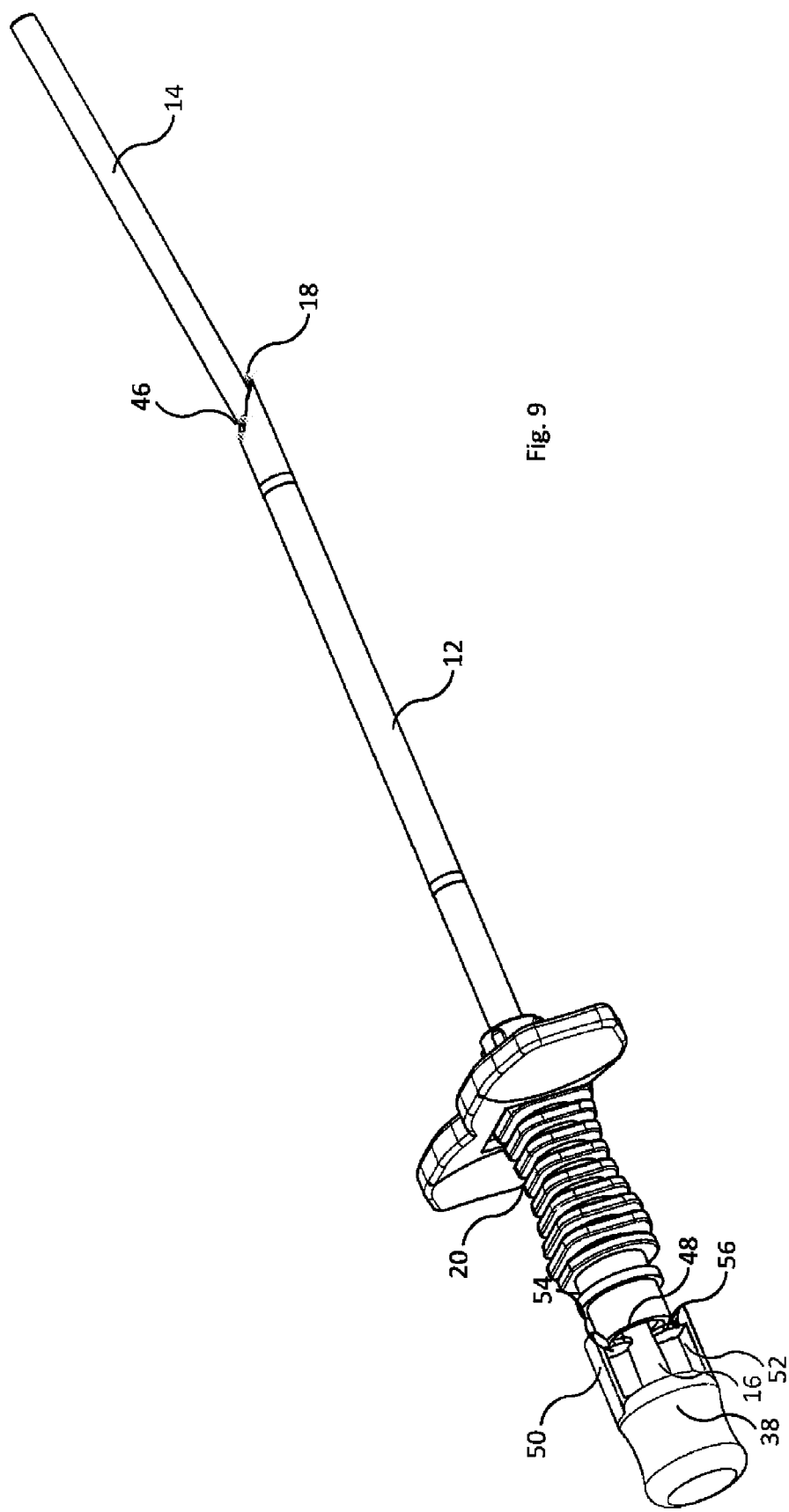
Figure 10:
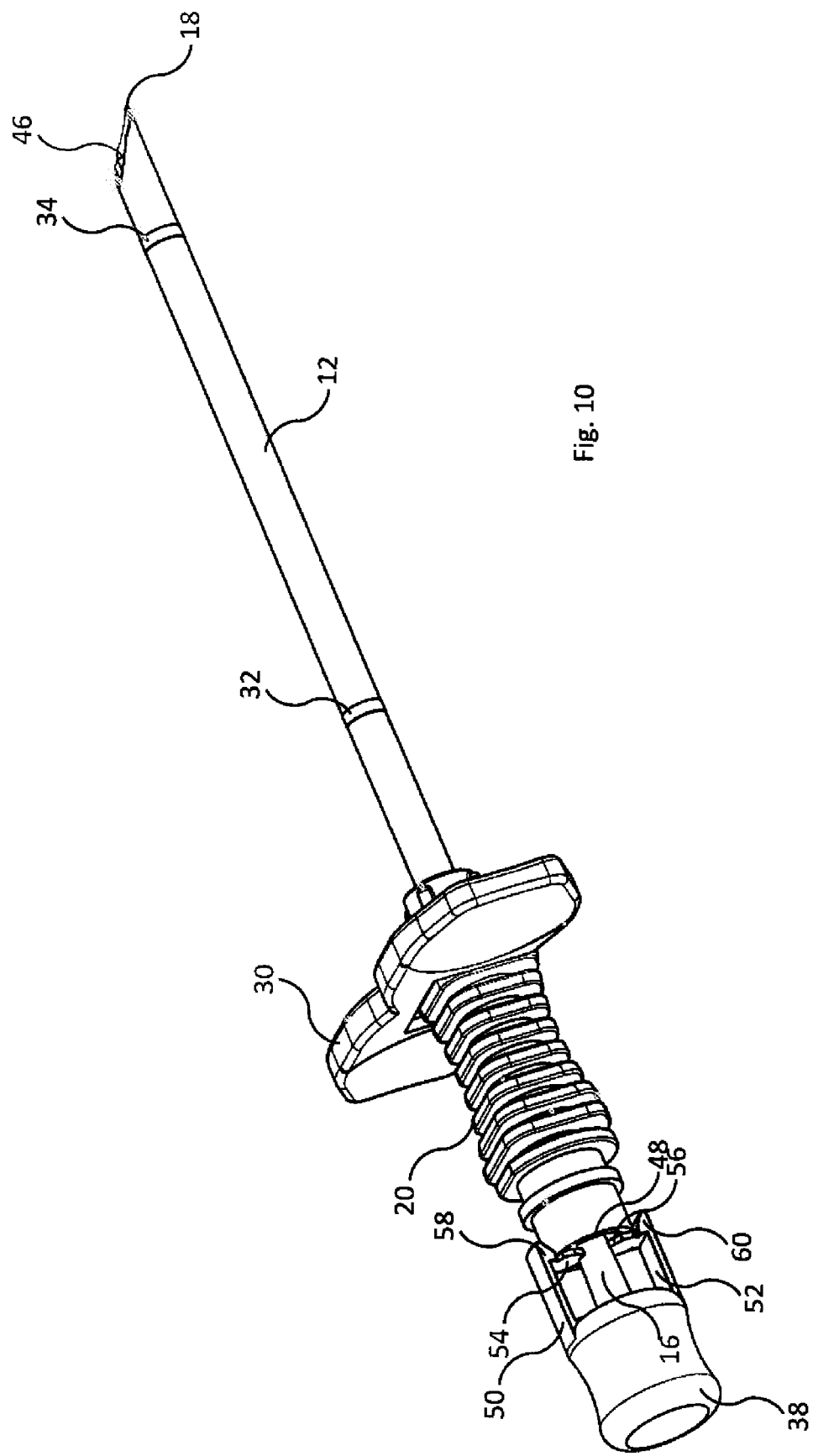
Figure 11:
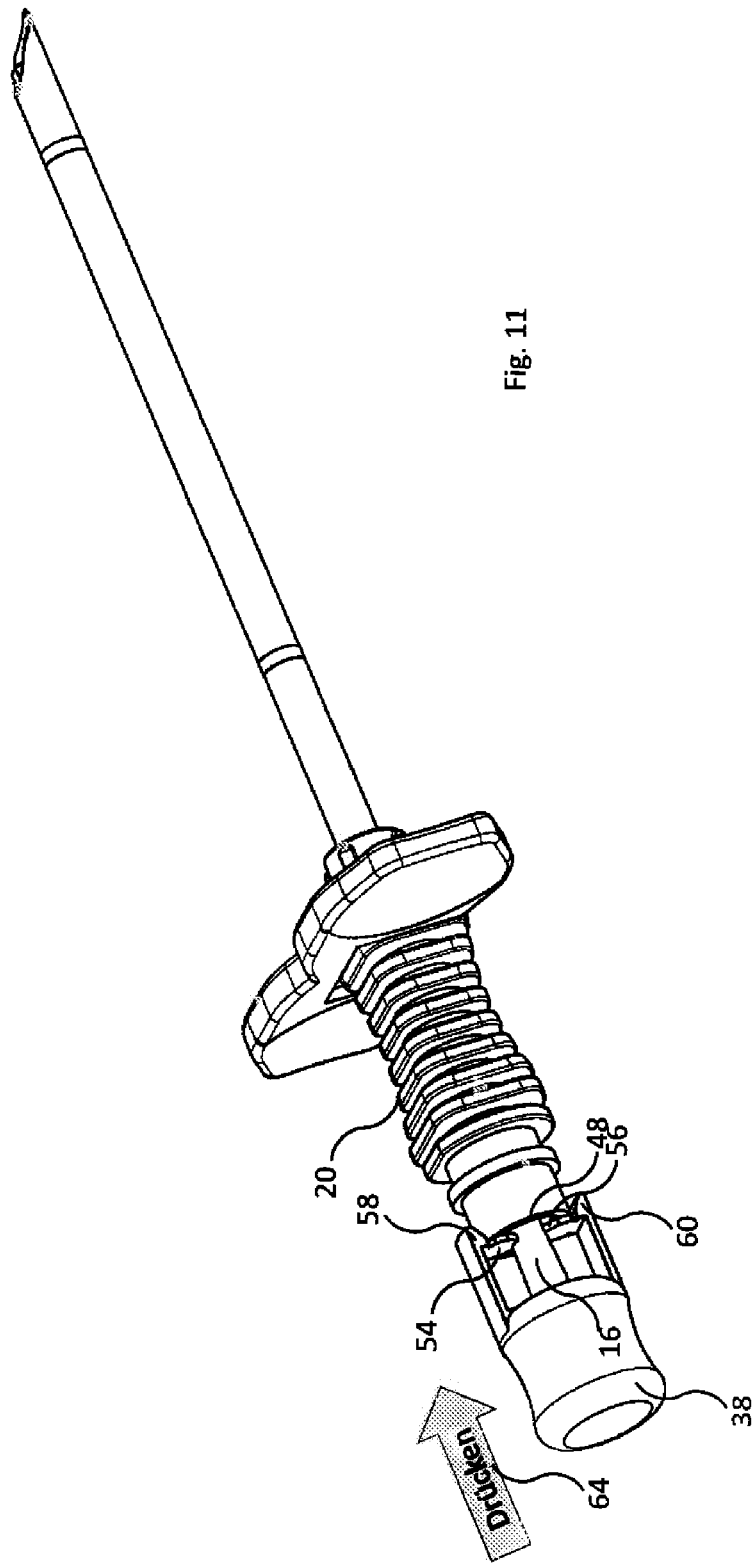
Figure 12:
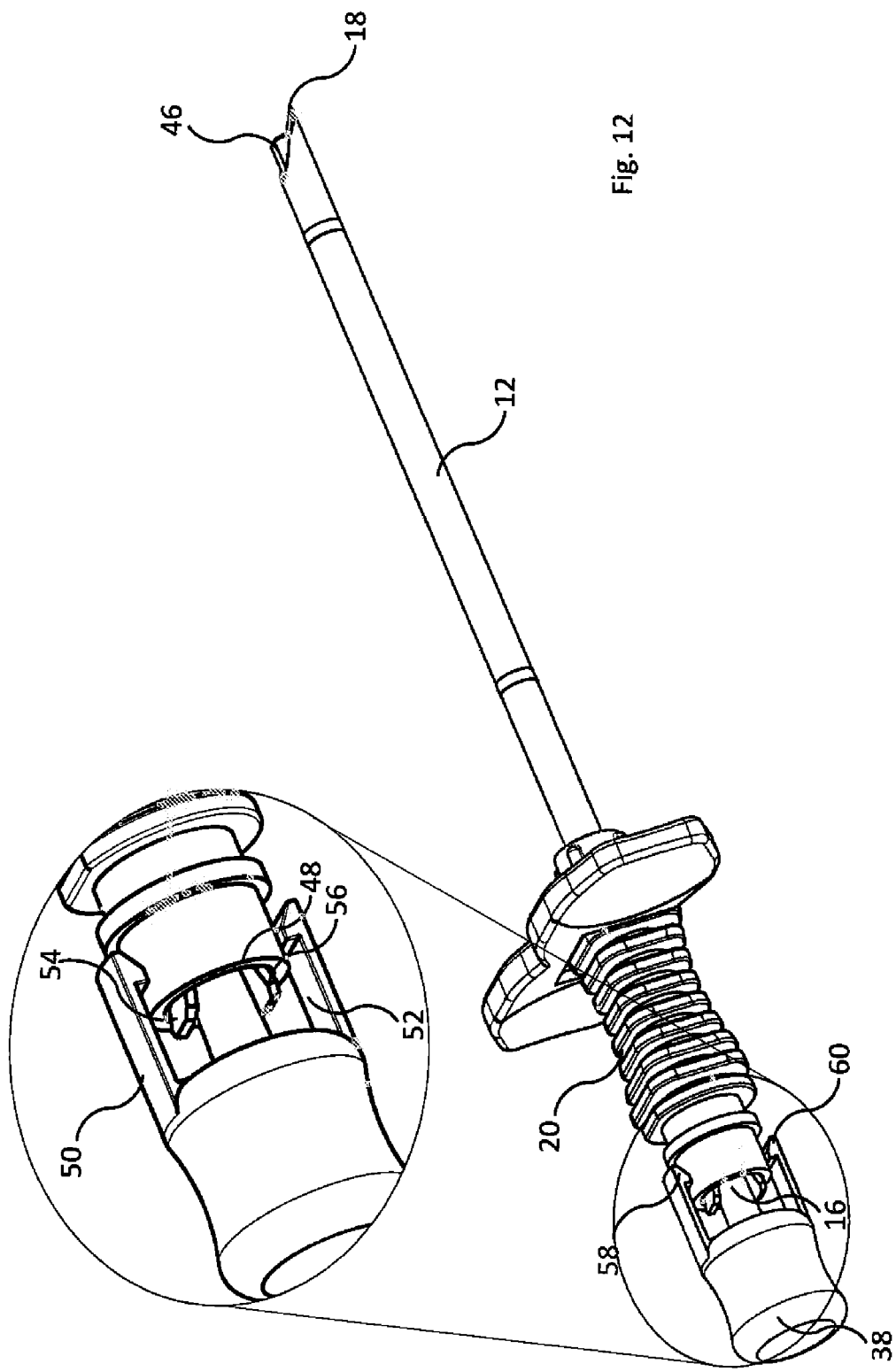
Figure 13:
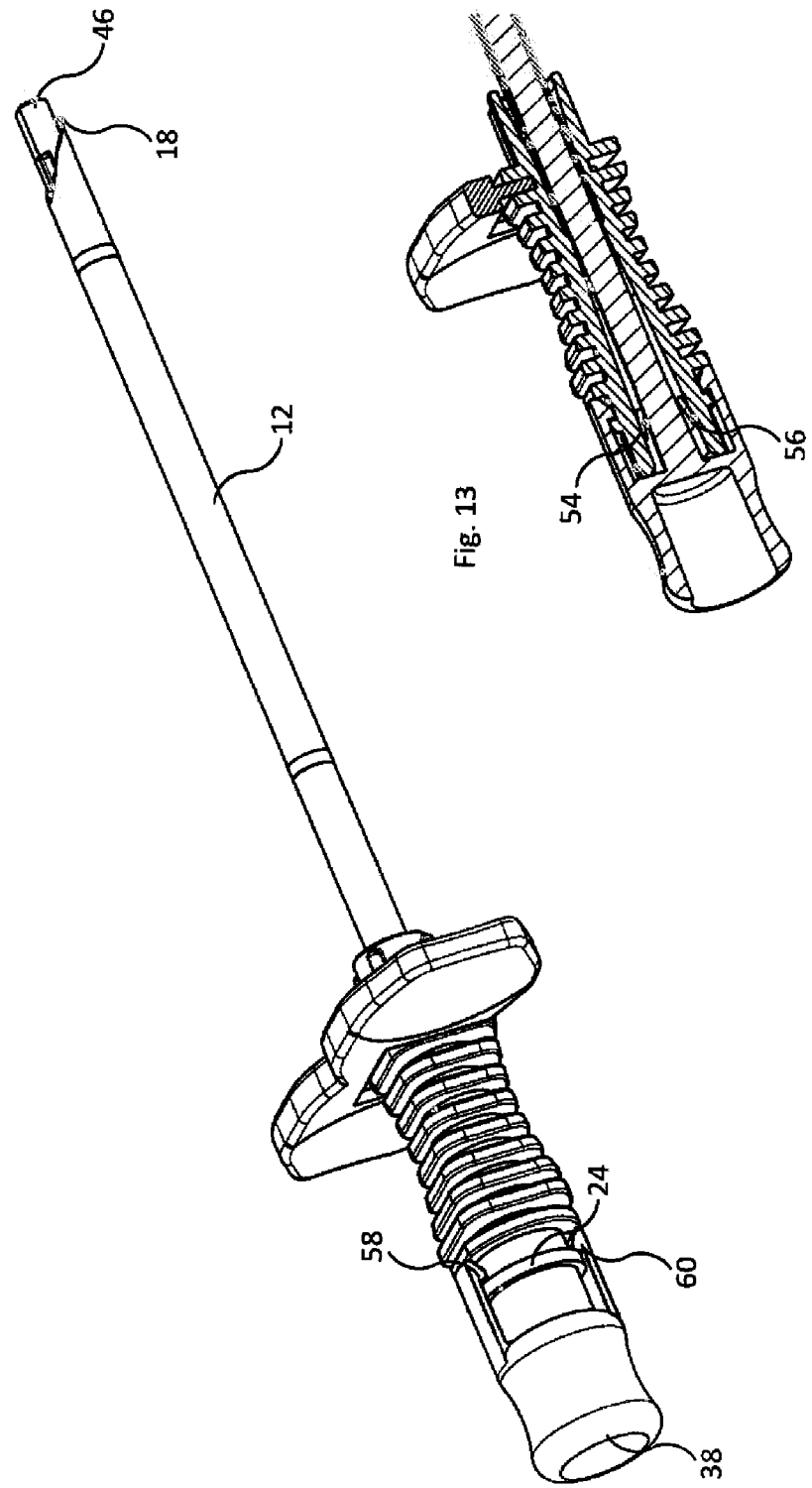
Figure 14:
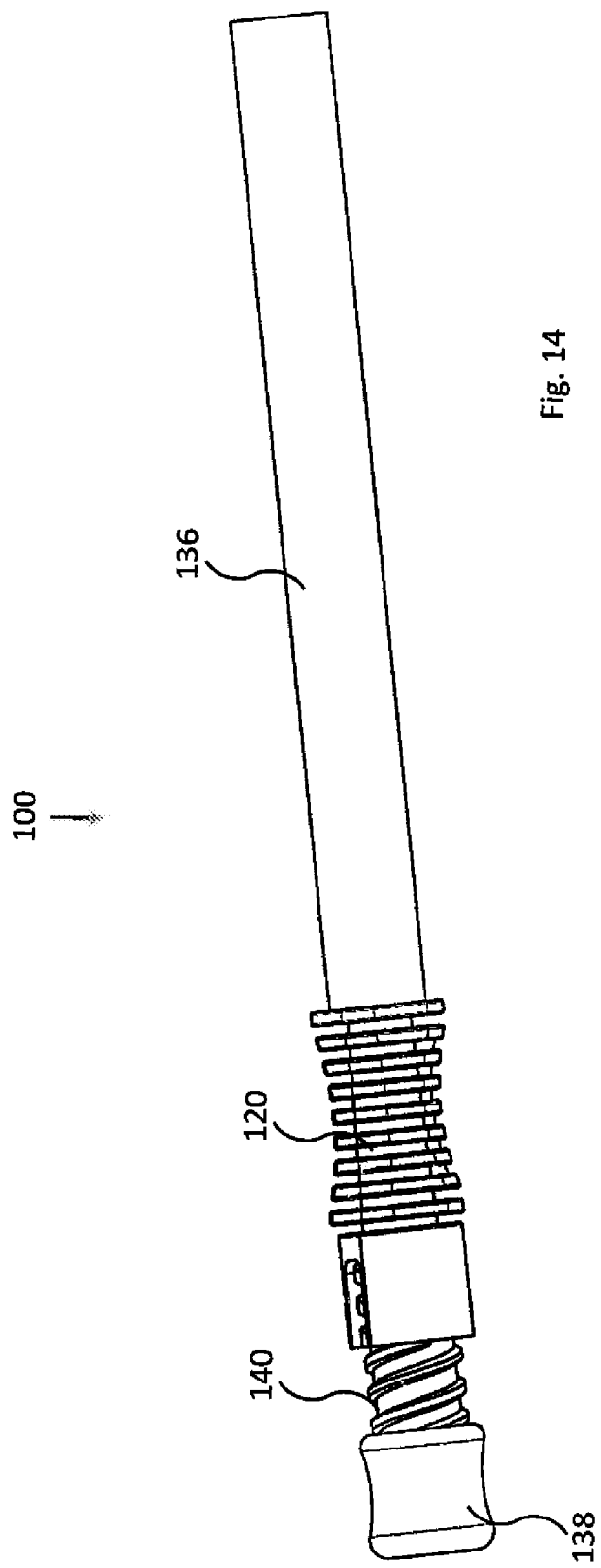
Figure 15:
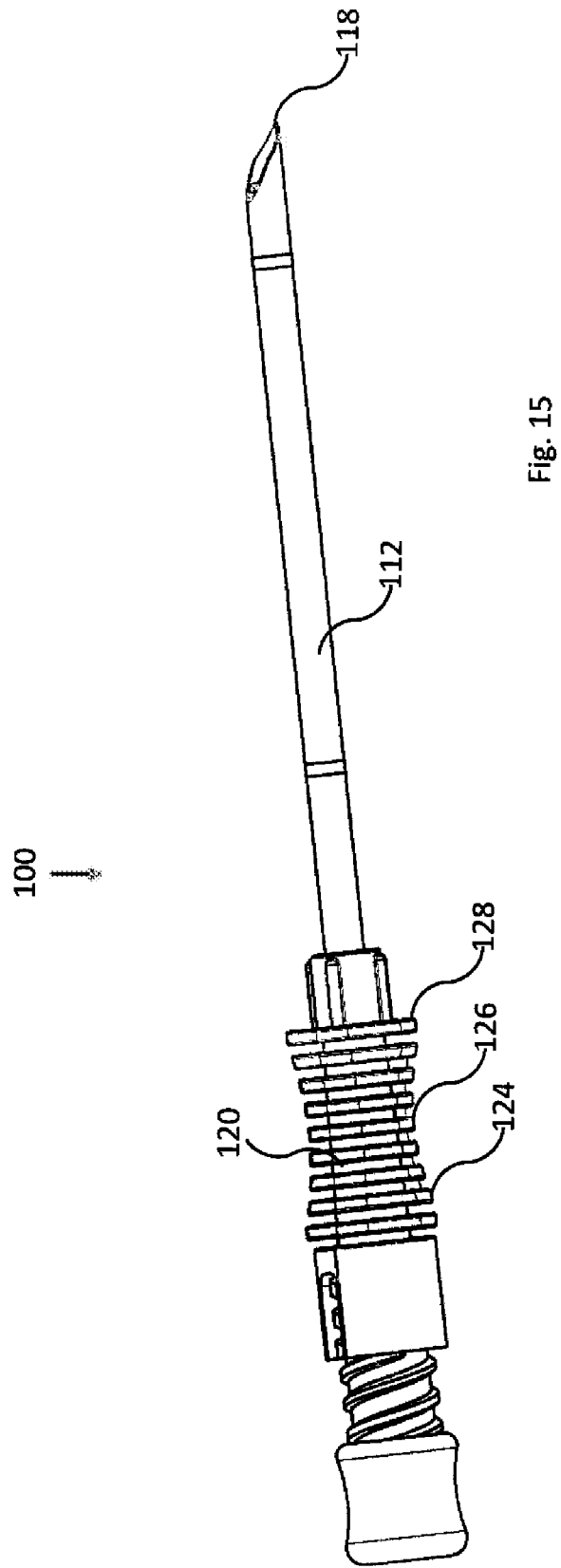
Figure 16:
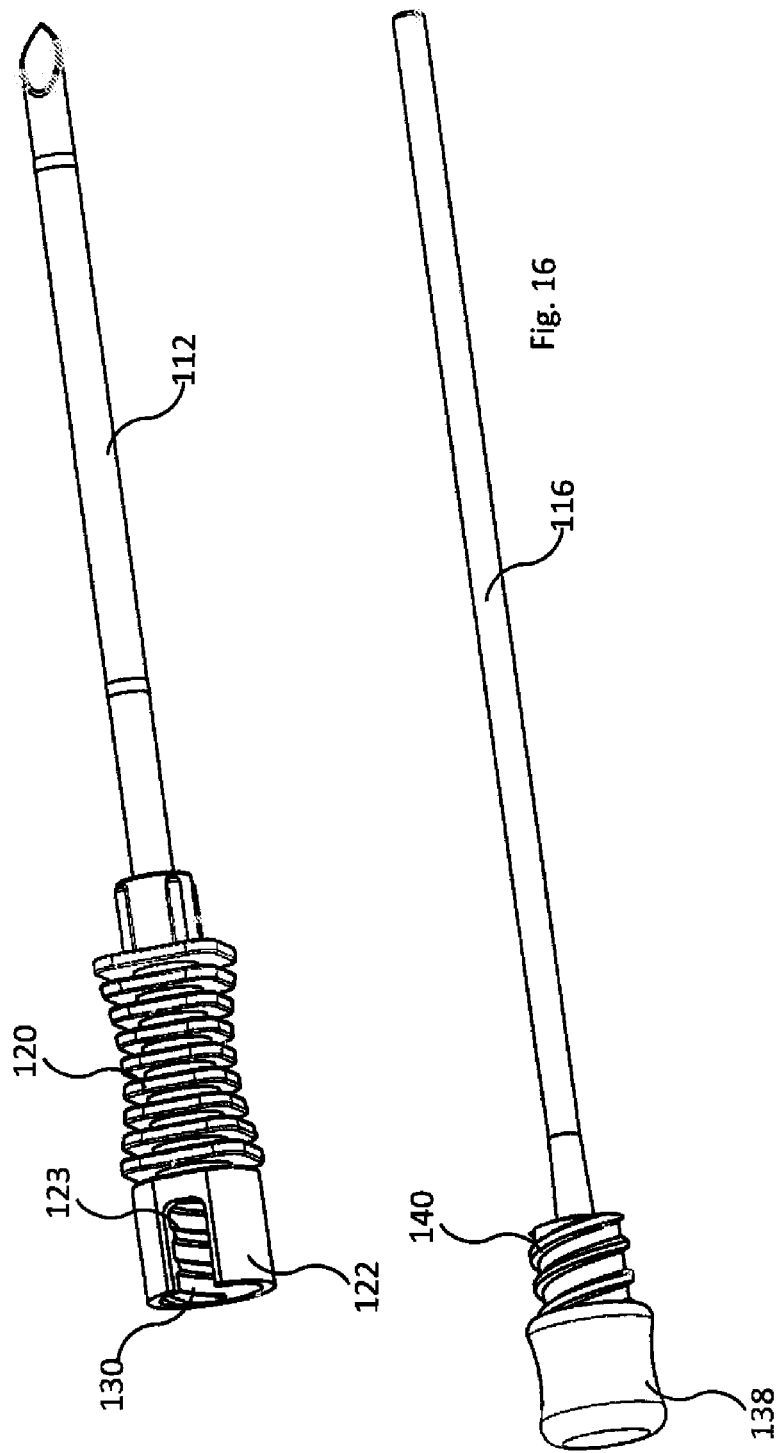
Figure 17:
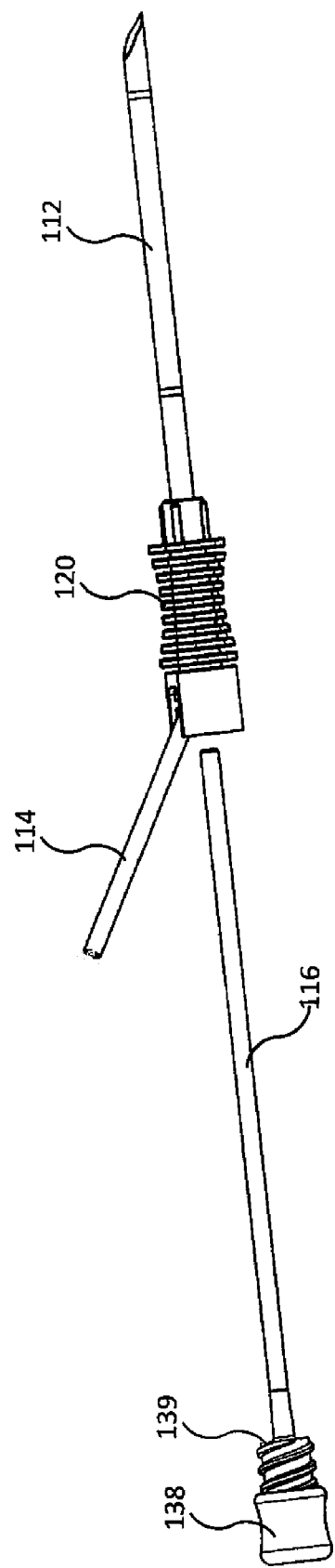
Figure 18:
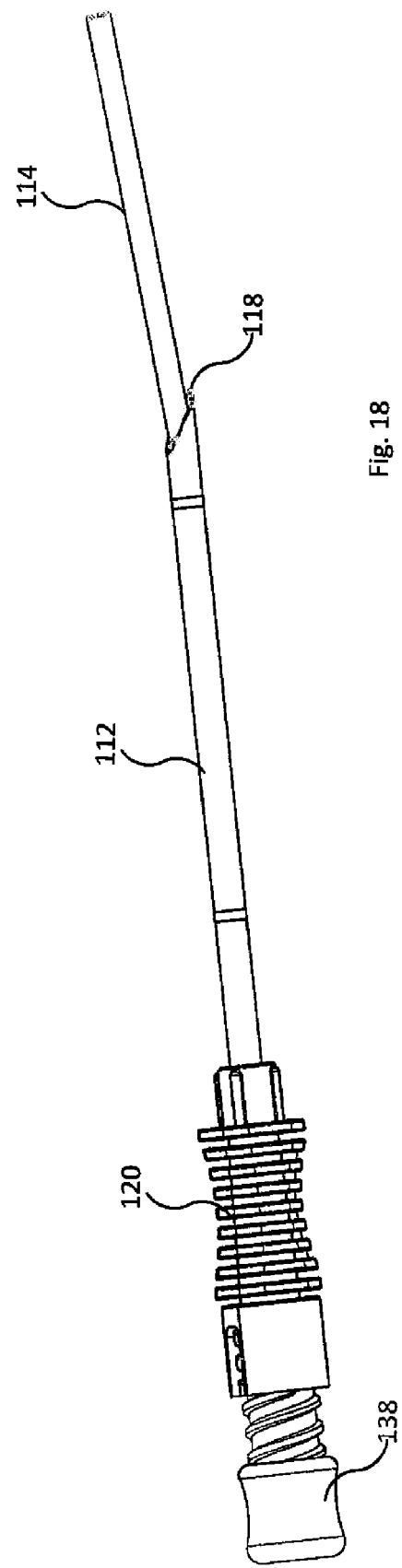
Figure 19:
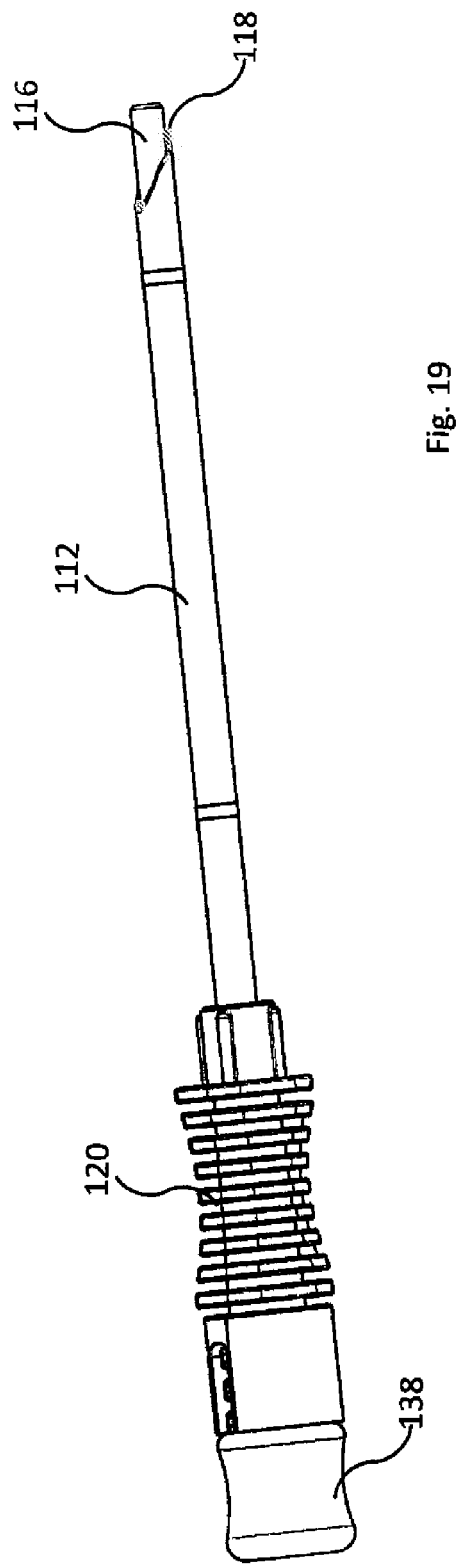

Further details, advantages and features of the invention are revealed not only by the claims and the features to be inferred therefrom, alone and/or in combination, but also by the preferred exemplary embodiment to be inferred from the following description of the drawings, in which:

FIG. 1 shows a cannula with protective sheath and plunger as delivered,

FIG. 2 shows the cannula with plunger according to FIG. 1, but with the protective sheath removed, FIG. 3 shows the illustration according to FIG. 2, but while the plunger is being withdrawn, FIG. 4 shows the cannula with plunger removed and details of the latter, FIG. 5 shows the cannula during insertion of an element to be deposited, FIG. 6 shows a schematic diagram explaining loading of the cannula with an element and a sectional representation of the latter, FIG. 7 shows the cannula with an element on introduction of the plunger and a sectional representation thereof, FIG. 8 shows the cannula with plunger before deposition of the element, FIG. 9 shows the cannula during deposition of the element, FIG. 10 shows the cannula with plunger after deposition of the element, FIG. 11 shows the cannula with plunger before activation of a safety mechanism, FIG. 12 shows the cannula with plunger moving towards locking, FIG. 13 shows the plunger locked together with the cannula or the extension thereof, FIG. 14 shows a further embodiment of a cannula with plunger and protective sheath as delivered, FIG. 15 shows the cannula with plunger according to FIG. 14, but with the protective sheath removed, FIG. 16 shows the cannula with the plunger removed, FIG. 17 shows the cannula in a position in which an element is being introduced therein and the plunger is aligned with the cannula, FIG. 18 shows the cannula with plunger during deposition of an element and FIG. 19 shows the cannula with the plunger covering the tip thereof.

FIGS. 1 to 13, in which identical elements are denoted with identical reference signs, reveal a device 10, in particular for depositing elements such as a solid medicament or implant, such as an identification or monitoring chip. The device 10 is used to this end with a cannula 12 for injecting the element 14 into a living organism and a plunger 16, also denoted stylet, by means of which the element 14 is pushed through the cannula 12.

FIG. 1 shows the device 10 as delivered.

FIG. 2 shows the cannula 12 which has a distal tip 18 and the proximal region of which is accommodated by an extension 20, which consists of a hollow-cylindrical base member 22, from the circumferential wall of which project ribs in the exemplary embodiment, some of which are identified with reference signs 24, 26, 28 (FIG. 3). A wing-like handle 30 is located in the distal region of the extension 20 to permit straightforward handling. In this respect, the cannula 12 with the extension 20 is of a sufficiently known design.

Markings 32, 34 for determining the depth of penetration of the cannula tip 18 into a living organism may be provided on the outer face of the cannula 12.

As delivered, the cannula 12 is surrounded by a protective sheath 36 which is pulled off prior to use. The protective sheath 36 may be connected, for example via predetermined breaking points, to the wing-like handle 30.

The plunger 16 has a proximal handle 38 for grasping it so that the plunger 16 can be pushed into and pulled out of the cannula 12. The latter proceeds when a plurality of elements are to be deposited in succession by means of the cannula 12.

Spaced from the handle 38, a plurality of projections 40, 42, 44, which are preferably evenly spaced around the circumference, originate from the circumferential surface of the plunger 16. The projections 40, 42, 44 enable retention of the plunger 16 within the cannula 12 by frictional engagement, such that it cannot slip out in uncontrolled manner during transport. The projections 40, 42, 44 are located in the proximal end region of the plunger 16 and thus of the cannula 12, when the plunger 16 has been pushed into the cannula 12 (FIG. 4).

While FIG. 1 shows the device 10 as delivered, in FIG. 2 the protective sheath 36 has already been pulled off.

FIG. 3 illustrates the position in which the plunger 16 is withdrawn from the cannula 12 in order to insert an element 14, as is apparent in principle from FIG. 5.

FIG. 4 shows a detailed view of the plunger 16 with handle 38 and the nub-like projections 40, 42, 44 by means of which the plunger 16 can be fixed in the cannula 12 by frictional engagement.

FIG. 5 shows a detailed view of how the element 14 is manually pushed into the cannula 12. A user can make use of his or her thumb to push the element 14 up to the proximal opening of the extension 20, such that, as shown in the lower illustration in FIG. 6, the element 14 comes to rest in part within the cannula 12.

In order to push the element 14 through the cannula 12 and then deposit it, once the element 14 has been inserted the plunger 16 is introduced, according to FIG. 7, into the proximal opening of the extension 20 in order to displace the element 14 in the longitudinal direction of the cannula 12 towards the tip 18.

In FIG. 8, the plunger 16 has already been pushed through the cannula 12 to such an extent that the element 14 projects with its distal end beyond the tip 18.

In FIG. 9, the plunger 16 has been pushed into the cannula 12 to such an extent that the element 14 can be deposited. To this end, the length of the plunger 16, strictly speaking of the plunger rod, and the cannula 12 with extension 20 are matched to one another such that the plunger 16 does not project with its distal end 46 beyond the tip 18, which originates from a ground bevel. In this position, the handle 38 of the plunger 16, with a limit stop originating therefrom, cooperates with the end edge 48, which extends on the opening side, of the extension 20. To this end, the handle 38 in the exemplary embodiment has two tab-like portions 50, 52 which run diametrically relative to the longitudinal axis of the plunger and may be denoted lugs and extend in the direction of the longitudinal axis of the plunger 16 and spaced therefrom, as is immediately apparent from the figures.

The tab-like portions 50, 52 originate from a base portion 51 with a cylindrical geometry of the handle 38, as is clearly apparent from the drawings. The base portion 51 may have a smaller diameter in its central region than at its edges so that it can be securely grasped without slippage.

The portions 50, 52, which may also be denoted vanes or lugs, are connected to the plunger 16 via connecting tabs 54, 56, i.e. very generally via connecting elements. A connection is here made such that the connecting tab 54, 56 is connected to the vane 50, 52 via a predetermined breaking point, while the connection between the connecting tab 54, 56 and the plunger 16 is made via a kind of film hinge. The connecting tabs 54, 56 here originate from hook-shaped projections 58, 60 which extend in the direction of the plunger 16 and extend from the ends of the vanes or lugs 50, 52 in the direction of the plunger 16. The hook-shaped projections 58, 60 here have a clearance which is approximately equal to the external diameter of the extension 20 in the region of the proximal opening thereof.

Obviously, it is no departure from the invention if the connecting tab 54, 56 is connected to the plunger 16 via a predetermined breaking point and to the retaining element 50, 52 via a film hinge.

If multiple elements 14 are to be deposited by means of the cannula 12, once one element 14 has been deposited, the plunger 16 is retracted to insert and then deposit a new element 14 in the manner previously described. The connecting tabs 54, 56, which may also be denoted limit stop elements, here act as limit stops, such that it is ensured that the tab-like retaining elements, i.e. the lugs 50, 52, serving as latching elements cannot interact with one of the ribs of the extension 20 in the manner described below and engage therebehind, whereby the plunger 16 would otherwise become latched, as is apparent from FIG. 13.

In order to enable such latching, a force must act on the handle 38 of the plunger 16 in the direction of the arrow 64 (FIG. 11) in such a manner that the connecting tabs 54, 56 previously serving as a limit stop are virtually sheared off in their connecting regions to the hook-shaped projections 58, 60 since the edge of the opening of the extension 20 acts on these regions. Notwithstanding this, the connecting tabs 54, 56 are not lost because according to the invention they remain articulatedly connected to the plunger 16 and, in accordance with FIG. 12, on penetration of the plunger 16 into the extension 20, i.e. into the passage opening thereof, are bent over in the direction of the plunger 16, such that the tabs 54, 56, while remaining connected to the plunger, remain in the interspace between the opening of the extension 20 and the plunger 16, as is apparent from FIG. 13. At the same time, the latching hooks 58, 60 in the exemplary embodiment engage behind the lowest or first rib 24 of the extension 20 of the cannula 12 (FIG. 13).

This is perceived not only haptically by a user. The connecting tabs 54, 56 breaking away from the tab-shaped retaining elements or lugs 50, 52 additionally generates perceptible noise which also indicates to the user that the safety function is initiated in order to latch the plunger 16 with the extension 20 by means of the lugs 50, 52 in such a manner that uncontrolled withdrawal from the cannula 12 is not possible.

It should be mentioned that the ribs 24, 26, 28 do not limit the invention. One or more other elements which originate from the extension 20 or are integrated therein may be provided in order to latch the plunger 16 when the device 10 is no longer to be used.

FIGS. 14 to 17 show a further embodiment of a device 100 with which, as with the device 10, an element 114 is to be deposited, while simultaneously ensuring that protection against injury during use of the device 100 is eliminated by structurally simple means. The intention is here to provide the possibility, in the event that the device is to be used for depositing solid medicaments or implants, of depositing a plurality of elements 114 successively in a body by means of the device 100.

FIG. 14 shows the device 100 as delivered and FIG. 15 shows it after removal of a protective sheath 136 surrounding the cannula 112.

As in the exemplary embodiment of FIGS. 1 to 13, the cannula 112 has a distal tip 118 and a proximal extension 120 which, in the exemplary embodiment, has ribs extending perpendicularly to the longitudinal axis of the cannula 112, some of which are identified with reference signs 124, 126, 128. It goes without saying that the ribs 124, 126, 128 are not a mandatory feature of the extension 120.

In the exemplary embodiment, in order to deposit an element 114, such as a solid medicament or implant, by means of the cannula 112, the element must be pushed through the cannula 112 and beyond the distal region. To this end, a plunger 116, which may also be denoted stylet and has a proximal handle 138, is used to allow the plunger 116 to be grasped and inserted into the cannula 112 and displaced in the direction of the longitudinal axis thereof.

According to the invention, the extension 120 has a proximal hollow-cylindrical portion 122 with internal thread 130. An external thread 140 matching the internal thread 130 is formed in the distal region of the handle 138, such that the handle 138 can be screwed together with the extension 120. This should proceed when, after deposition of the solid medicament 114, the cannula 112 is no longer to be used and the tip 118 thereof is to be covered by the distal end region of the plunger 116, as is apparent from FIG. 19. The length of the plunger 116 is here matched with the length of the cannula 112 with its extension 120 in such a way that, when the handle 138 is screwed into the extension 120 and is preferably latched together therewith in the end position, the distal end region of the plunger 116 projects beyond the tip 118, as is apparent from FIG. 19.

The device according to the invention 100 offers the user two defined positions between the plunger 116 and cannula 112. The first position is that in which the handle 138, i.e. the distal edge region 139 thereof, abuts against the start of the internal thread 130, i.e. no rotational motion has occurred between the handle 138 and the extension 120. In this position, as is apparent from FIG. 18, the plunger 116 has been displaced within the cannula 112 to an extent such that the solid medicament 114 can be deposited.

The second position is obtained when the handle 138 and extension 120 have been screwed together, wherein when the handle 138 is completely screwed into the extension 120, a locking element such as a protrusion is first overcome bringing about latching, such that an opposing screw movement is no longer possible with the result that the cannula tip 118 remains covered by the plunger 116, thus eliminating any risk of injury to the user.

As is apparent from the figures, the proximal hollow-cylindrical portion 122 has a slot 123 extending in the direction of the longitudinal axis of the cannula 112, via which the solid medicament 114 can be introduced.

While the exemplary embodiment shows the handle 138 with external thread 140 and the extension 120 with internal thread 130, it goes without saying that it is also possible to select a design in which the handle 138 has a distally extending hollow-cylindrical portion with an internal thread which interacts with an external thread or with tabs of the extension 120 in order to enable a screw connection.

The invention claimed is:

1. A device for depositing an element, comprising:
   a cannula having a distal end and a proximal end,
   a tip disposed at the distal end of the cannula, and
   an extension accommodated at a proximal region of the cannula,
   wherein the extension comprises one or more ribs extending transversely to the longitudinal axis of the cannula, and a plunger with a handle which is displaceable in part within the cannula,
   wherein the handle has tab-like retaining elements extending in the longitudinal direction of the plunger, and extending spaced from the plunger, and
   wherein each one of the retaining elements is connected to the plunger via a connecting element having a first end region and second end region, and
   wherein at least one of the first end region and the second end region is severable by interaction with the extension.

2. The device according to claim 1, wherein the connecting element is severably connected to the retaining element, and articulatedly connected to the plunger, or vice versa.

3. The device according to claim 1, wherein the connecting elements interact as a limit stop with a proximal edge of the extension.

4. The device according to claim 1, wherein the retaining element has a latching portion extending in the direction of the plunger.

5. The device according to claim 1, wherein, with the distal end of the plunger projecting beyond the tip of the cannula and the plunger latched, the connecting elements are separated from the retaining elements and, while remaining connected to the plunger, are oriented along the plunger.

6. The device according to claim 1, wherein the latching portions engage behind a latching element of the extension.

7. The device according to claim 1, wherein, with the distal end of the plunger projecting beyond the tip of the cannula and the plunger latched, the connecting elements are separated from the plunger and, while remaining connected to the retaining elements, are oriented therealong.

8. The device according to claim 1, wherein the connecting elements are severable both from the plunger and from the retaining elements by interaction with the extension.

9. The device according to claim 1, wherein the connecting element is connected to the latching portion.

10. The device according to claim 1, wherein a proximal region of the extension comprises a hollow-cylindrical portion with an external diameter D, and in that the clearance between two latching portions diametrically opposed with regard to the longitudinal axis of the plunger is equal or approximately equal to D.

11. The device according to claim 1, wherein the retaining elements originate from a base portion of the handle of the plunger which has a cylindrical outer geometry in its end regions.

12. The device according to claim 1, wherein the retaining elements on the outside transition flush into the circumferential surface of the base portion.

13. The device according to claim 1, wherein the connecting element is connected via a film hinge to the plunger, or to the retaining element.

14. The device according to claim 1, wherein at least one projection which enables frictional engagement with the inner surface of the cannula projects out from the plunger.

15. The device according to claim 14, wherein the at least one projection projects out from a proximal region of the plunger.

16. The device according to claim 1, wherein a plurality of projections, uniformly distributed around the circumferential wall, project out from the plunger.

17. The device according to claim 1, wherein the plunger with the handle is a plastics injection moulding.

18. A device for depositing an element, including a solid medicament or implant, comprising:
    a cannula with a tip disposed at a distal end of the cannula, and an extension accommodated at a proximal region of the cannula, wherein the extension optionally has one or more ribs extending transversely to the longitudinal axis of the cannula, and a plunger with a handle which is displaceable in part within the cannula,
    wherein the handle is connectable to the extension via a screw connection, and the length of the plunger is matched with the length of the cannula in such a way that:
    in a first position, in which, in the absence of a screw fastening, but with the extension and the handle in contact, the tip is uncovered by the plunger, and
    in a second position, in which the extension and the handle are screwed together, and latched together by overcoming a locking element, an opposing screw movement between the extension and the handle is not possible, and a distal end region of the plunger covers the tip to prevent any risk of injury by the tip.

19. The device according to claim 18, wherein the handle has an external thread which interacts with an internal thread present in the extension.

20. The device according to claim 14, wherein the handle has an internal thread which interacts either with tabs projecting out from the extension, from the proximal edge region thereof, or with an external thread of the extension.

21. The device according to claim 18, wherein the locking element is a projection.

22. The device according to claim 21, wherein the projection is a shoulder.

23. The device according to claim 18, wherein at least one projection which enables frictional engagement with the inner surface of the cannula projects out from the plunger.

24. The device according to claim 23, wherein the at least one projection projects out from a proximal region of the plunger.

25. The device according to claim 18, wherein a plurality of projections, uniformly distributed around the circumferential wall, project out from the plunger.

26. The device according to claim 18, wherein the plunger with the handle is a plastics injection moulding.

* * * * *